United States Patent
Heller et al.

(10) Patent No.: US 6,746,582 B2
(45) Date of Patent: Jun. 8, 2004

(54) ELECTRODES WITH MULTILAYER MEMBRANES AND METHODS OF MAKING THE ELECTRODES

(75) Inventors: Adam Heller, Austin, TX (US); Ting Chen, Austin, TX (US); Keith A. Friedman, Austin, TX (US)

(73) Assignee: TheraSense, Inc., Alameda, CA (US)

(*) Notice: Subject to any disclaimer, the term of this patent is extended or adjusted under 35 U.S.C. 154(b) by 115 days.

(21) Appl. No.: 09/854,310

(22) Filed: May 11, 2001

(65) Prior Publication Data

US 2001/0054319 A1 Dec. 27, 2001

Related U.S. Application Data

(60) Provisional application No. 60/203,762, filed on May 12, 2000.

(51) Int. Cl.[7] .................... G01N 27/327; G01N 21/00; G01N 31/22; B05D 3/00
(52) U.S. Cl. ..................... 204/403.06; 204/403.05; 422/57; 427/2.13
(58) Field of Search .................. 204/403.04, 403.05, 204/418, 403.06; 422/52, 56, 57, 82.05, 82.06; 427/2.13; 205/778, 793

(56) References Cited

U.S. PATENT DOCUMENTS

| | | | |
|---|---|---|---|
| 4,871,442 A | * 10/1989 | Yamaguchi et al. | 204/418 |
| 4,943,364 A | 7/1990 | Koch et al. | 204/415 |
| 5,006,314 A | * 4/1991 | Gourley et al. | 422/82.07 |
| 5,075,127 A | * 12/1991 | Yafuso et al. | 427/2.11 |
| 5,611,900 A | 3/1997 | Worden et al. | 204/403.1 |
| 5,696,314 A | 12/1997 | McCaffrey et al. | 205/778 |
| 5,773,270 A | 6/1998 | D'Orazio et al. | 204/403.01 |
| 5,804,048 A | 9/1998 | Wong et al. | 204/403.09 |
| 6,015,480 A | 1/2000 | Craig et al. | 204/418 |
| 6,162,611 A | * 12/2000 | Heller et al. | 435/14 |

FOREIGN PATENT DOCUMENTS

| | | |
|---|---|---|
| EP | 0 352 610 A2 | 1/1990 |
| EP | 409033 A | * 1/1991 |
| WO | WO 94/10553 | 5/1994 |

OTHER PUBLICATIONS

Villeneuve et al. ("Electrochemical Detection of Nitric Oxide Production in Perfused Pig Coronary Artery: Comparison of the Performances of Two Electrochemical Sensors," Journal of Pharmacological and Toxicological Methods (1998), 40(2), 95–100).*

Derwent abstract of EP 0409033 A2 (Schaffar).*

Derwent abstract of JP 62266192 A (Tokyo Ohka Kogyo Co. Ltd.).*

Bourdillon, C. et al., "Catalysis and Mass Transport in Spatially Ordered Enzyme Assemblies on Electrodes", *J. Am. Chem. Soc.*, vol. 117, No. 46, pp. 11499–11506 (1995).

Caruso, F. et al., "2. Assembly of Alternating Polyelectrolyte and Protein Multilayer Films for Immunosensing", *Langmuir*, vol. 13, No. 13, pp. 3427–3433 (1997).

Kobayashi, Y. et al., "Alternate Deposition of Cationic and Anionic Polymers for the Improvement of Response Characteristics of Glucose Biosensor", *Electrochemistry*, vol. 67, No. 12, pp. 1147–1149 (Dec. 1999).

Lvov, Y. et al., "Assembly of Multicomponent Protein Films by Means of Electrostatic Layer–by–Layer Adsorption", *J. Am. Chem. Soc.*, vol. 117, No. 22, pp. 6117–6123 (1995).

Sun, Y. et al., "Chemically Modified Electrode via Layer–by–Layer Deposition of Glucose Oxidase (GOD) and Polycation–bearing Os Complex", *Thin Solid Films*, vol. 327–329, pp. 730–733 (1998).

* cited by examiner

Primary Examiner—Alex Noguerola
(74) Attorney, Agent, or Firm—Merchant & Gould P.C.

(57) ABSTRACT

A sensor including a sensing layer is disposed over an electrode or an optode and a layer-by-layer assembled mass transport limiting membrane disposed over the sensing layer. The membrane includes at least one layer of a polyanionic or polycationic material. The assembled layers of the membrane are typically disposed in an alternating manner. The sensor also optionally includes a biocompatible membrane.

23 Claims, 8 Drawing Sheets

ELECTRODES WITH MULTILAYER MEMBRANES AND METHODS OF MAKING THE ELECTRODES

This application claims the benefit of U.S. Provisional Patent Application Serial No. 60/203,762, filed May 12, 2000, incorporated herein by reference.

GOVERNMENT SUPPORT

This invention was made with government support under grant No. 3R01DK42015 from the NIH-NIDDK. The government has certain rights in the invention.

FIELD OF THE INVENTION

This invention relates to sensors and sensor components that have multilayer membranes and methods of making and using the sensors and sensor components. In addition, the invention relates to enzyme electrodes and optodes with multi-layer analyte-flux limiting membranes and methods of making and using the optodes and the electrodes.

BACKGROUND OF THE INVENTION

Miniature biosensors utilizing enzyme-containing optodes and electrodes for monitoring biochemicals often include mass-transport controlling membranes. The membranes can affect some or all of the characteristics of the optodes or electrodes, including their sensitivity, size, apparent stability, dynamic range and selectivity. Micro-membranes for use with miniature biosensors typically cannot be easily cut to size from preformed membranes and if cut by a precision tool, such as a laser or an electron beam, their placement on and attachment to the surface of an electrode or optode can be difficult.

The reproducible casting of micro-membranes can also be difficult. For cast micro-membranes, the pore sizes and their distribution are typically determined by the relative rates of nucleation and mass-transport during generation of the membrane by phase separation as a result of solvent evaporation. The outcome of the simultaneously occurring nucleation and the mass transport processes depends on the evolution (meaning the time-dependence during the solvent evaporation) of the viscosity, the concentrations of the solvent and the non-solvent, and the membrane's leached phase and its residual phase. These are affected by time-dependent temperature gradients and by the time-dependent gradient of the partial pressure of the evaporating solvent over a droplet, the dimensions of which shrink and are a function of the time-dependent contact angle with the wetted surface.

SUMMARY OF THE INVENTION

Generally, the present invention relates to electrodes and optodes having membranes to reduce analyte flux or reduce interferent flux or both. One embodiment is a sensor that includes a sensing layer disposed on a substrate and a multilayer flux-limiting membrane disposed over the sensing layer. The membrane includes a first layer disposed on and bound to the sensing layer and one or more additional layers disposed on and bound to the preceding layers of the membrane. The substrate can have a conductive material upon which the sensing layer is disposed to form an electrode or an optical material, such as an optical fiber, upon which the sensing layer is disposed to form an optode. As an example, the membrane includes at least two layers; one of which is a polycationic layer or a polyanionic layer. Optionally, the membrane includes at least one layer that has functional groups that can capture transition metal ions.

Another embodiment is a method of making a sensor. A sensing layer is disposed on a substrate. A first membrane layer is disposed on and binds to the sensing layer. One or more subsequent membrane layers are disposed over the first membrane layer, each of the subsequent membrane layers binding to the immediately preceding membrane layer. For example, the membrane layers can be formed by chemisorption or reactive adsorption.

The above summary of the present invention is not intended to describe each disclosed embodiment or every implementation of the present invention. The Figures and the detailed description which follow more particularly exemplify some but not all of these embodiments.

BRIEF DESCRIPTION OF THE DRAWINGS

The invention may be more completely understood in consideration of the following detailed description of various embodiments of the invention in connection with the accompanying drawings, in which.

Figure 1:
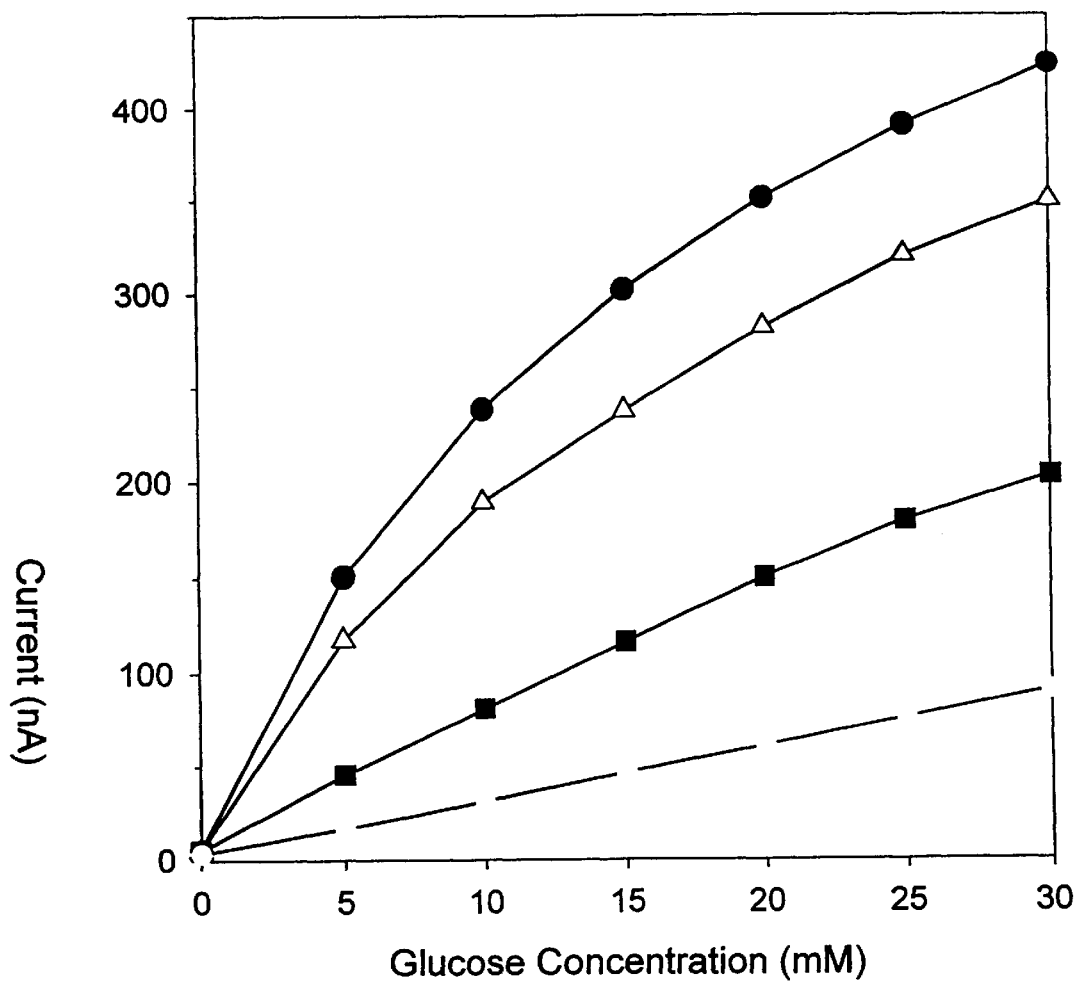
FIG. 1 is a graph illustrating the dependence of the sensitivity of a glucose sensing electrode on the number of PAc/PAm/PAc/PAm/PAc/PVPEA sextets: (dashed line) none; (squares) one; (triangles) two; (circles) three.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

The present invention is believed to be applicable to sensors, particularly miniature sensors, and methods of making and using the sensors. In particular, the present invention is directed to membranes for electrodes and optodes for use in sensors and methods of making and using the electrodes and optodes. While the present invention is not so limited, an appreciation of various aspects of the invention will be gained through a discussion of the examples provided below.

A sensor includes an electrode or optode. Each electrode or optode includes a substrate. For an electrode, the substrate includes a conductive material that is typically either formed on a non-conductive support (e.g., a polymeric film) or as a wire, rod, plate, or other object. A sensing layer (e.g., transducing layer) is provided over at least a portion of the conductive material to transduce the flux of a chemical, usually a biochemical, termed the analyte to an electrical signal, such as a current flowing through the electrode. An optode can include, for example, an optical fiber (or other optical substrate) at the tip of which a layer of a biologically active macromolecule is provided (preferably, immobilized). The sensing layer on the optode converts the change in the concentration of the analyte to a change in photon flux.

The electrode or optode is covered with a membrane. The purpose of the membrane is to reduce analyte-flux or reduce or prevent interferent flux to the electrode or a combination of these features. The membrane contains at least two layers, and, typically, at least six layers. At least one of the layers includes a layer containing a polyanion or a polycation and the polyanionic or polycationic layer is disposed over the sensing layer. When operating to reduce flux of an analyte, interferent, or other material, the membrane typically provides a thin zone in which the solubility of a solute (e.g., analyte or interferent) is lower by at least an order of magnitude than it is in the sample solution. A membrane having such a zone is referred to as "mass transport limiting". The cross sectional area of the sensor through which mass transport is limited is defined as the "active area". The active area of the sensors in at least some embodiments of this invention is 0.1 cm$^2$ or smaller. For example, sensors can be formed with active areas between 10$^{-2}$ cm$^2$ and 10$^{-8}$ cm$^2$. Membranes having mass transporting areas (e.g., "active areas") between 10$^{-3}$ cm$^2$ and 10$^{-5}$ cm$^2$ are particularly useful for biosensing applications.

The membrane can be formed, for example, by sequential chemisorption of layers. Preferably, each particular layer, other than the terminal top layer, binds both the preceding and succeeding layers of the membrane. Generally, two consecutive layers are not identical; however, layers made of the same material but differently (for example, oppositely) oriented can be disposed next to each other. The layers typically form an array of bonds as a result of ionic, hydrophobic, coordinative, covalent, van der Waals, or hydrogen bonding interactions between the materials of the two layers. For example, the membrane can be formed of alternating polyanionic and polycationic layers.

In one embodiment, a micro-membrane is formed in-situ on a miniature enzyme electrode by disposing (e.g., chemisorbing or otherwise depositing) a polyanionic material on a polycationic surface of the electrode, rinsing, disposing a polycationic on the polyanionic material, rinsing, and repeating the cycle a desired number of times. It will be understood that a similar procedure can be used with a polyanionic surface of the electrode by first depositing a polycationic material followed by a polyanionic material and repeating the cycle a desired number of times. Other orders of layers can also be used.

In particular, the membranes are useful in those biosensors that function by chemically converting (e.g., reacting) a chemical or biochemical. The chemical or biochemical can be, for example, an analyte that is being assayed, a product formed by reaction of the analyte, a co-reactant of the analyte, a product or reactant of a reaction that is catalyzed or inhibited by the presence of the analyte, or a constituent whose attachment to an optode or electrode is accelerated or inhibited by the presence of the analyte.

As an example, membranes of the invention can be fanned on, and are evaluated in the Examples below for, miniature glucose oxidizing or electrooxidizing electrodes. For these electrodes, glucose is typically converted to gluconolactone in the first step of a detection reaction. Suitable miniature glucose electrodes include, for example, those disclosed in U.S. Pat. Nos. 5,262,305; 5,262,035; 5,264,104; 5,593,852; 5,665,222; 6,143,164; 6,120,676; 6,576,101; 6,134,461; 6,338,790, and U.S. patent application Ser. No. 09/434,026, now U.S. Pat. No. 6,616,819, all of which are incorporate herein by reference. It will be appreciated that electrodes forte detection of analytes other than glucose can also benefit from the use of the membranes described herein. Glucose electrodes are illustrated herein as an application example.

Glycemia has been monitored amperometrically in the subcutaneous interstitial fluid with miniature electrodes for some time. The electrode reactions applied in such monitoring include (a) the mediated electrooxidation of glucose to gluconolactone at electrodes coated with a redox mediator (e.g., a redox polymer which electrically "wires" the reaction centers of glucose oxidase to an electrode) (Equations 1a and 1b, below) or, alternatively, (b) the glucose oxidase catalyzed reaction of glucose with O$_2$, to produce gluconolactone and H$_2$O$_2$ (Equation 2a, below), followed either by electro-oxidation of the H$_2$O$_2$ (Equation 2b, below), or by monitoring the change in the O$_2$ partial pressure or concentration.

glucose+2 bound mediator(ox)→gluconolactone+2 bound mediator(red)+2H$^+$     (1a)

2 bound mediator (red)→2 bound mediator(ox)+2e$^-$     (1b)

glucose+O$_2$→gluconolactone+H$_2$O$_2$     (2a)

H$_2$O$_2$→O$_2$+2H$^+$+2e$^-$     (2b)

The current at the electrode generally scales with the flux of glucose to the electrode. The flux, and therefore also the current, typically increases linearly with the glucose concentration as long as the entire glucose flux at the electrode is consumed in the electrode reaction.

Figure 8:
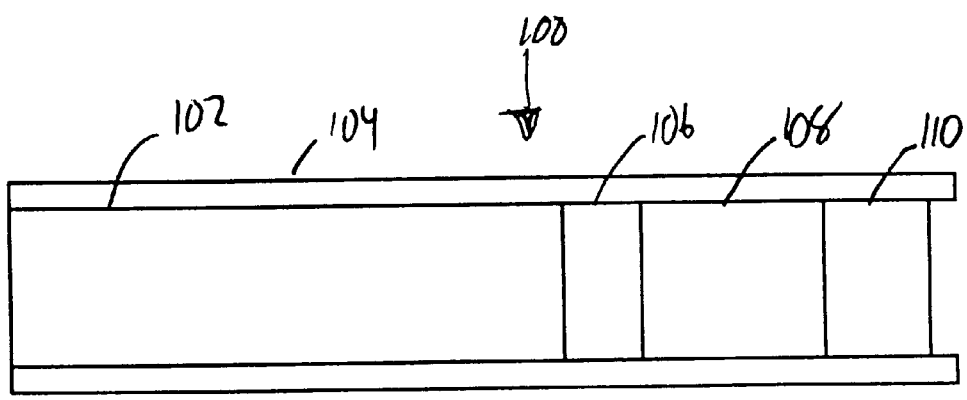
FIG. 8 is a schematic cross-sectional view of one embodiment of an electrode, according to the invention.

FIG. 8 illustrates one example of a suitable electrode 100. The electrode includes a conductive material 102 within an insulating sleeve 104. Disposed on the conductive material 102 are a sensing layer 106, a membrane 108, and a biocompatible layer 110. Examples of similar electrode configurations, together with examples of some suitable sensing layers and biocompatible layers are provided in U.S.

Pat. No. 5,593,852. Other suitable sensing layers and biocompatible layers are described, for example, in U.S. Pat. Nos. 5,665,222; 6,143,164; 6,120,676; 6,576,101; 6,134,461; 6,338,790, and U.S. patent application Ser. No. 09/434,026, now U.S. Pat. No. 6,616,819, all of which are incorporated by reference.

The conductive material 102 can be, for example, carbon, a metal, or a conductive compound or polymer. The insulating sleeve 104 is typically formed from an insulating compound or polymer. In one method of manufacture, a tip of a metal wire (e.g., a gold wire) is etched to form a recess within the insulating sleeve where the sensing layer 106, membrane 108, and biocompatible layer 110 are deposited.

The sensing layer 106 typically provides a mechanism for transducing an analyte flux (or the flux of a product molecule formed or consumed by a reaction of the analyte) to an electrical signal. The sensing layer can contain, for example, a redox mediator to facilitate the indirect or direct transfer of electrons between the conductive material and the analyte. One type of redox mediator is a transition metal complex or compound (e.g., an osmium, ruthenium, or iron complex or compound). The redox mediator can be a monomeric redox compound or complex. but is preferably in a non-leachable form, such as a redox polymer. The redox polymer, has a polymeric backbone with multiple redox centers. Examples of suitable redox mediators are disclosed in, for example. U.S. Pat. Nos. 5,262,305; 5,262,035; 5,264,104; 5,593,852; 5,665,222; 6,143,164; 6,120,676; 6,576,101; 6,134,461; 6,338,790, and U.S. patent application Ser. No. 09/434,026, now U.S. Pat. No. 6,616,819, all of which are incorporated by reference.

The sensing layer 106 can also include a second electron transfer agent, such as an enzyme. The second electron transfer agent can catalyze the electrochemical oxidation or reduction of the analyte. As an example, suitable second electron transfer agents for glucose include glucose oxidase or glucose dehydrogenase; for lactate, lactate dehydrogenase; and for hydrogen peroxide, peroxidase.

The biocompatible layer 110 prevents the penetration of large biomolecules into the electrodes. This can be accomplished by using a biocompatible layer 110 having a pore size that is smaller than the biomolecules that are to be excluded. Such biomolecules can foul the conductive material 102 or the sensing layer 106 thereby reducing the effectiveness of the electrode 100 and altering the expected signal amplitude for a given analyte concentration. The biocompatible layer 110 may also prevent protein adhesion to the electrode 100, formation of blood clots, and other undesirable interactions between the electrode 100 and body. A preferred biocompatible coating is a hydrogel, which contains at least 20 wt. % fluid when in equilibrium with the analyte-containing fluid. Examples of suitable hydrogels are described in U.S. Pat. No. 5,593,852, incorporated herein by reference, and include crosslinked polyethylene oxides, such as polyethylene oxide tetraacrylate.

The preferred membrane 108 includes at least three, and typically at least six, twelve, or eighteen layers. One example of a membrane 108 is formed using alternating polycationic and polyanionic layers. Typically, these layers are formed using polymers. Suitable polycationic polymers include, for example, polyallylamine hydrochloride (PAm), poly(4-vinylpyridine) quaternized by reacting about one third to one tenth of the pyridine nitrogens with 2-bromoethylamine (PVPEA), polyethylene imine, and polystyrene modified with quaternary ammonium functions. Suitable polyanionic polymers include, for example, poly (acrylic acid) (PAc), poly(methacrylic acid), partially sulfonated polystyrene, polystyrene modified with functions having carboxylate anions, and DNA (deoxyribonucleic acid) or RNA (ribonucleic acid) strands, fragments or oligomers. The membrane 108 can serve one or more functions including, for example, a) limiting glucose flux or b) reducing or eliminating the flux of interferents to the electrode. Glucose sensors will be described as an example, but sensors can be formed for other analytes using the same principles.

In glucose sensing optodes or electrodes, a glucose flux-limiting membrane can enhance one or more properties of the optode or the electrode including, for example, expanding the dynamic range, enhancing the apparent stability and improving the selectivity for glucose which may enable one-point calibration of an implanted electrode.

Reducing the flux of glucose (or any other analyte) using a membrane can expand the dynamic range of a sensor. The upper limit of the dynamic range of the sensor is that glucose concentration where the entire influx of the analyte is still consumed. When this limit is exceeded, the rate of glucose-conversion is slower than the influx and the sensor "saturates": the current no longer increases when the glucose concentration is raised. The kinetic limit, represented by the current density at the glucose concentration above which it no longer increases, is an intrinsic property of the electrode. This current density typically scales linearly with the rate of the slower of reactions 1(a) or 1(b) for a mediator-comprising glucose oxidase electrode or the slower of reactions 2(a) or 2(b) in an $O_2$—utilizing electrode. Because the membrane does not affect the intrinsic rate of the slowest step, its insertion between the assayed fluid and the electrode expands the upper limit of the dynamic range.

Typically, the sensor's apparent stability, which is the stability perceived by its user, can also be improved upon insertion of the glucose flux limiting membrane. The user remains unaware of the deterioration of the electrode's chemistry as long as the kinetics of the slowest step remains fast enough to convert all the influx of glucose to a current. Furthermore, the more blocking the membrane is, the better the apparent stability will typically be. The increased apparent stability and the upward extension of the dynamic range are gained at the cost of reduced specific sensitivity, defined as the current per unit area at unit glucose concentration. The specific sensitivity decreases because less glucose reaches the reactive zone on the electrode. When the specific sensitivity decreases, a larger glucose-transporting area may be needed for the sensor's current to reach an easily measured value.

The membrane thus defines, at least in part, (a) the lowest analyte concentration where the current is large enough to be easily measured and the highest analyte concentration above which the electrode's current no longer increases with the concentration of the analyte; (b) the extent of the feasible miniaturization of the sensor; and (c) the apparent stability of the sensor. Fitting of these characteristics to those sought in the intended application requires tailoring of the flux-controlling membrane. While the characteristics of the earlier solvent-cast membranes depended on the spreading of the casting solution, and on the gradients of temperature and of solvent partial pressure near the membrane being formed; the characteristics of the membranes formed according to the invention typically do not depend on these factors. As a result, the simultaneous tailoring of their many desired characteristics is typically easier.

Figure 3:
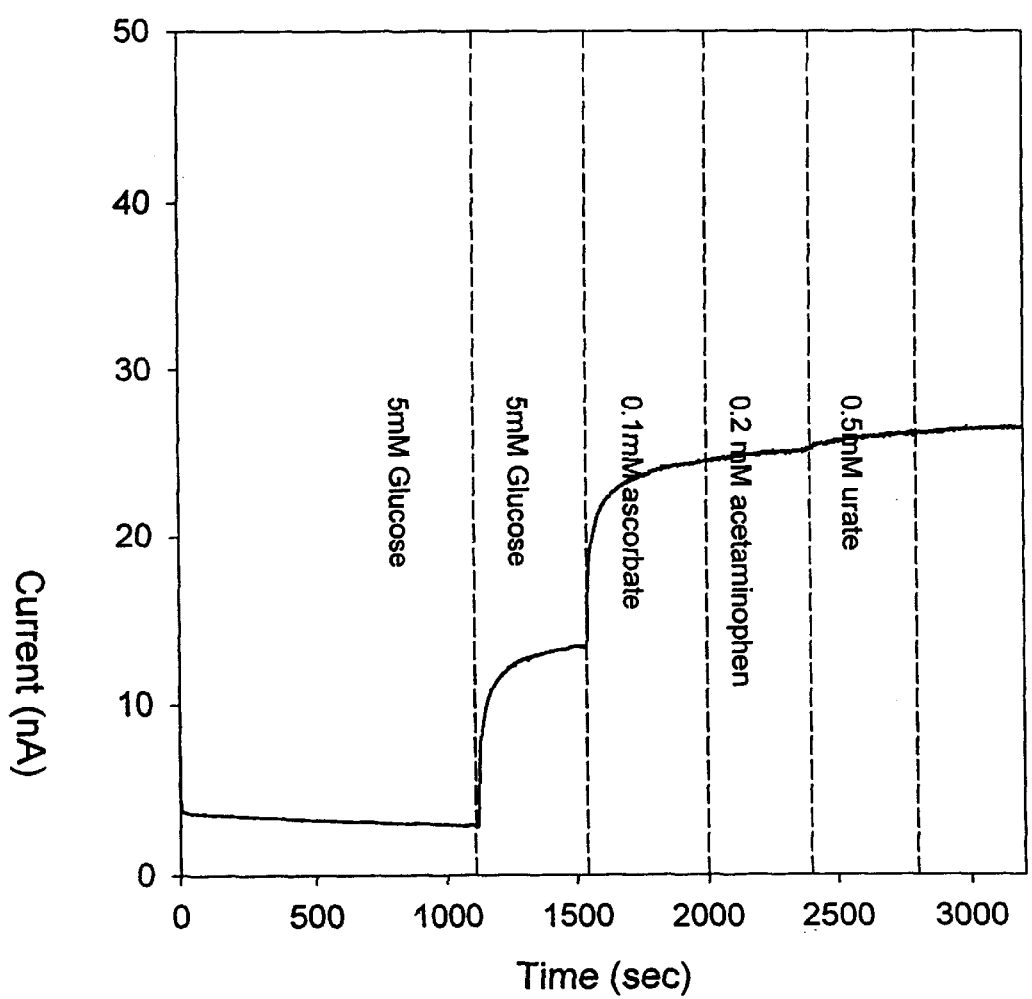
FIG. 3 is a graph illustrating current increments upon raising the concentrations sequentially by 5 mM glucose, 5 mM glucose, 0.1 mM ascorbate, 0.2 mM acetaminophen and 0.5 mM urate.

In at least some embodiments, the membrane also reduces or eliminates the flux of interferents to the conductive material of the electrode. The bias resulting from the presence of an interferent that is rapidly electrooxidized at the applied potential is defined by its flux to the electrode surface. In the absence of a membrane, the flux is controlled by diffusion in the solution and is defined by the diffusivity and the concentration of the interferent. When a membrane is inserted between the solution and the electrode, the % bias is defined by the ratio of the products of the solution concentrations and permeabilities of the interferent and glucose.

$$\% \text{bias} = \frac{C_{I,S} \cdot D_{I,S}}{C_{G,S} \cdot D_{G,S}} \times 100\% \text{ (solution)}$$

$$\% \text{bias} = \frac{C_{I,S} \cdot P_{I,M}}{C_{G,S} \cdot P_{G,M}} \times 100\% \text{ (membrane)}$$

$$P_{I,M} = K_{I,M} D_{I,M} / l_M = \frac{C_{I,M}}{C_{I,S}} \times D_{I,M} / l_M$$

where C is the concentration of the interferent (I) or glucose (G) in the solution (S) or membrane (M), D represents the appropriate diffusivity, P represents the partition coefficient, and IM represents the thickness of the membrane. Because the permeability is a product of the concentration of the diffusing species in the membrane and of its diffusivity in the membrane, the % bias increases linearly with the ratio of the partition coefficients of the interferent and of glucose between the membrane and the solution. When only monovalent anionic species (Cl⁻, ascorbate, urate) are present, the concentration of anions in the polycationic POs-EA membrane of the sensing layer equals the concentration of its cationic charges, which is about an order of magnitude higher than the concentration of anions in the solution. As a result, the sensing layer is permselective for anions over glucose and in the absence of a neutral or polyanionic glucose-flux-controlling membrane (e.g. Nafion™) the flux and electro-oxidation current of 0.1 mM ascorbate could equal or exceed 10% of that of 10 mM glucose. The membranes described herein are not typically permselective for anions. As a result, ascorbate or urate is not preferentially electrooxidized. As seen in FIG. 3, at 10 mM glucose concentration the combined % bias resulting of the presence of 0.1 mM ascorbate, 0.2 mM acetaminophen and 0.5 mM urate is less than 5%, even though the sensor is poised at 450 mV (Ag/AgCl), a potential where acetaminophen is not rapidly electrooxidized, but ascorbate and urate are.

Transition metal ions also influence the sensor readings. Transition metal ions reduce the intrinsic kinetic capacity of the enzyme layer to electrooxidize glucose and thereby severely reduce the dynamic range and the sensitivity. (See FIG. 4) The loss is attributed to both inhibition of the enzyme and a reduction in the surface density of electroactive redox centers caused by excessive crosslinking through coordination of pyridine rings of neighboring redox centers. In the Examples, a transition metal ion capturing PVPEA/PAc bilayer is included in the membrane. The addition of the PVPEA layer provides an alternative site for capture of transition metal ions by providing pyridine functionalities that can complex with the transition metal ions. It will be recognized that other materials can be used in place of PVPEA. Typically, the replacement materials will include functionalities that can form complexes with the transition metal ions. Because the PVPEA layer is already highly crosslinked, the incremental crosslinking by coordination of the transition metal ions does not change excessively the permeability of the micro-membrane to glucose.

As an example, described in the Examples section below, membranes were assembled by sequentially chemisorbing polyanionic and polycationic materials on miniature ($5 \times 10^{-4}$ cm²) enzyme electrodes. The sequential chemisorption process allowed the simultaneous tailoring of their sensitivity, dynamic range, drift and selectivity. When assembled on tips of 250 μm diameter gold wires coated with a redox polymer/glucose oxidase sensing layer, they allowed tailoring of the glucose electrodes for greater than 2 nA/mM sensitivity; 0 to 30 mM dynamic range; drift of ≦5% per 24 hours at 37° C. at 15 mM glucose concentration; ≦5% current increment by the combination of 0.1 mM ascorbate, 0.2 mM acetaminophen and 0.5 mM urate. The membranes also retained transition metal ions that otherwise bind to and damage the redox polymer and the enzyme. The electrodes were tested in the jugular veins and in the intrascapular subcutaneous region of anaesthetized and heparinized non-diabetic Sprague-Dawley rats, in which rapid changes of glycemia were forced by intravenous glucose and insulin. After one-point in-vivo calibration of the electrodes, all of 152 data points were clinically accurate when it was assumed that after insulin injection the glycemia in the subcutaneous fluid lags by 9 minutes behind that of blood withdrawn from the insulin-injected vein.

EXAMPLES

The following are the materials used to make the electrodes: Glucose oxidase (GOx) (Fluka, Milwaukee, Wis., EC 1.1.3.4, 197 units/mg) from *Aspergillus niger*; poly (ethylene glycol) diglycidyl ether (400) (PEGDGE), and polyallylamine hydrochloride (MW 50,000) (PAm) from Polysciences, Warrington, Pa.; and polyacrylic acid sodium salt (PAc) (MW 15,000), 1-[3-(dimethylamino)propyl]-3-ethylcarbodiimide (EDC), and N-hydroxysuccinimide (NHS) from Aldrich, Milwaukee, Wis. The redox polymer, poly (4-vinylpyridine) partially N-complexed with [Os (bpy)$_2$ Cl]$^{+/2+}$ and quaternized with bromoethylamine (POs-EA), was prepared as described in Gregg et al., *J. Phys. Chem.* 95, 5970 (1991), incorporated herein by reference. The related polymer from which the osmium complex was omitted, PVPEA, was prepared by quaternizing poly(4-vinylpyridine) with bromoethylaamine.

Example 1

Formation of Glucose Electrodes. Miniature gold electrodes were structurally similar to those described in Csöregi et al., *Anal. Chem.* 66, 3131 (1994) and U.S. Pat. No. 5,593,852, both of which are incorporated herein by reference. The electrodes were made of polyimide-insulated 0.25 mm gold wire, which was cut to 5 cm long pieces. At one end, the insulation was stripped from 0.5 cm of the wire to make the electrical contact. At the other end, a 90 μm deep polyimide-walled recess was formed by electrochemically etching away the gold under galvanostatic control by an EG&G PARC 273A potentiostat/galvanostat.

The tip of the gold wire at the bottom of the shielded recess was coated with the transduction (sensing) layer; a micro-membrane; and a biocompatible layer. The first and third layers were formed by micropipetting polymer solutions onto the gold surface under a microscope, using a micromanipulator. The micro-membrane was formed by dip and rinse cycles.

The sensing layer included the redox polymer POs-EA and GOx crosslinked with PEGDGE. A 20 mg/mL solution of GOx were dissolved in a 0.1 M sodium bicarbonate aqueous solution. The GOx solution was then mixed at 2:1 volume ratio with a 12 mg/mL solution of sodium periodate and the mixture was reacted in the dark at room temperature for 1 hour. 2 μL of the now periodate-oxidized GOx solution was mixed with 16 μL of 10 mg/mL POs-EA solution and 1.4 μL of 2.5 mg/mL PEGDGE solution. 15 droplets of about 5 nL mixed solution were sequentially micropipetted into the recessed cavity formed by back-etching the gold in its polyimide insulation. The resulting films were cured at 45° C. for 30 minutes.

The micro-membrane was formed over the sensing layer. The polyelectrolyte solutions 20 mM PAc, 20 mM PAm and 20 mM PVPEA (the concentrations being those of the acidic or the basic functions, not of the macromolecules) were prepared in 0.1 M NaCl buffered at pH 6 with 0.1 M 2-[N-morpholino] ethanesulfonic acid (MES). This buffer was used also to prepare 20 mM EDC and 50 mM NHS. The sensors were coated by dipping and rinsing cycles, alternately in PAc and in PAm, to form PAc/PAm bilayers, or in PAc then in PVPEA to form the PAc/PVPEA bilayers. The sequence of the resulting sextets was PAc/PAm/PAc/PAm/PAc/PVPEA; the slashes (/) representing rinses with MES buffer to remove the excess (unbound) polyelectrolyte. All of the sensors used in vitro and in animals, except for those made for the parametric optimization of the sensors, had three of the sextet layers (18 layers total).

The biocompatible layer was formed over the micro-membrane. The biocompatible layer was formed by UV-photocrosslinking tetraacrylated PEO, using 2,2-dimethoxy-2-phenyl-acetophenone as the photoinitiator.

Example 2

In Vitro Experiments using the Electrode of Example 1. In vitro experiments were carried out in a stirred, water-jacketed electrochemical cell in 0.15 M NaCl, 0.02 M phosphate buffer solution with pH 7.1. The cell had a saturated Ag/AgCl reference electrode, a platinum counter electrode and the modified 0.25 mm gold wire tip working electrode, as described in Example 1. Unless otherwise stated the working electrode was poised at 400 mV vs. Ag/AgCl, and the cell was maintained at 37° C. with an isothermal circulator (Fisher Scientific, Pittsburgh, Pa.). The potential was controlled by a CHI832 electrochemical detector (CH Instrument, Austin, Tex.) and a PC collected the data.

FIG. 1 illustrates the dependence of the sensitivity on the number of PAc/PAm/PAc/PAm/PAc/PVPEA sextets where the dashed line indicates no micro-membrane, the squares indicate one sextet, the triangles indicate two sextets, and the circles indicate three sextets. This demonstrates the expansion of the linear range and the corresponding decrease in sensitivity when an increasing number of counter-charged polyelectrolyte layers is applied on the sensing layer. When the micro-membrane consisted of two sextets (of the sequence PAc/PAm/PAc/PAm/PAc/PVPEA/PAc/PAm/PAc/PAm/PAc/PVPEA) the current increased linearly with the glucose concentration at least up to 30 mM. As seen in FIG. 1, the linear domain in-vitro now extended through the entire physiologically relevant 2–30 mM range.

Figure 2:
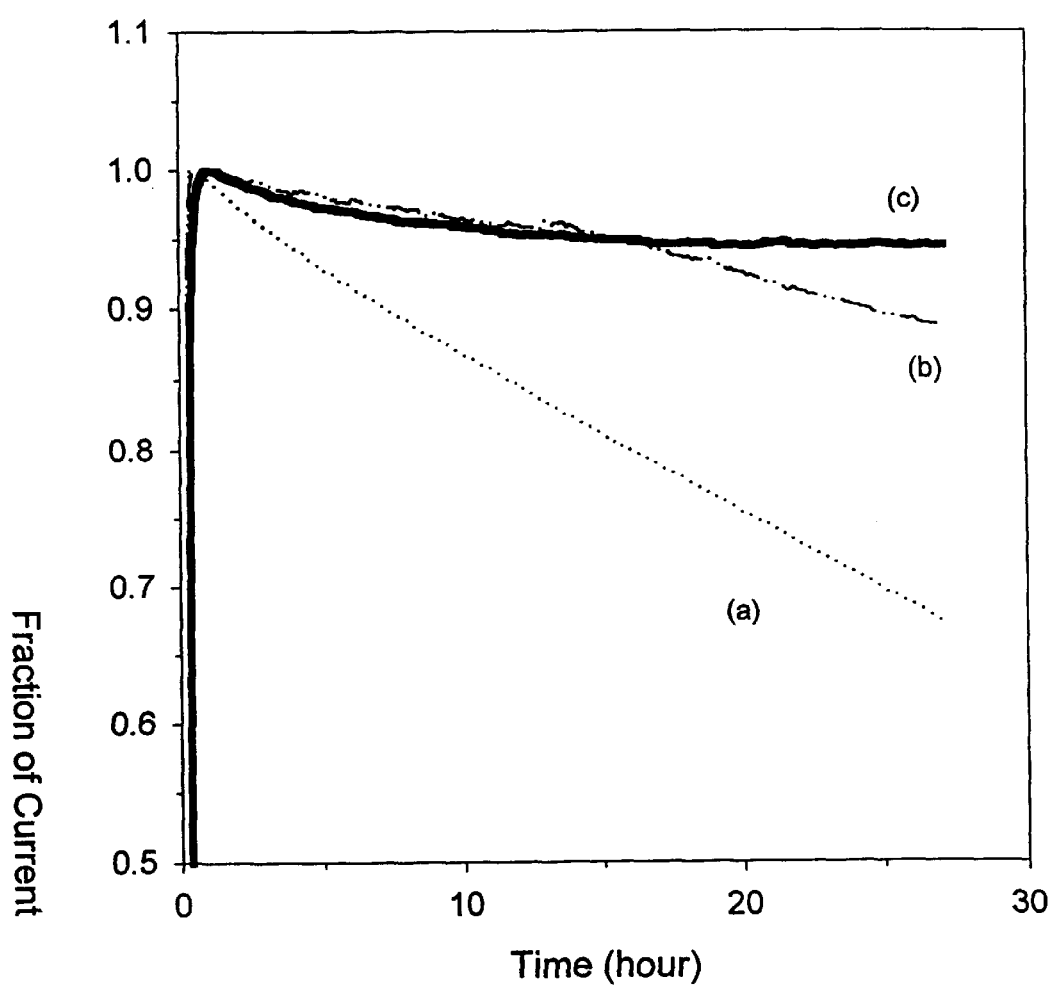
FIG. 2 is a graph illustrating dependence of the apparent stability of a glucose sensing electrode on the number of PAc/PAm/PAc/PAm/PAc/PVPEA sextets: (a) none; (b) two; (c) three.

FIG. 2 illustrates the dependence of the apparent stability on the number of PAc/PAm/PAc/PAmn/PAc/PVPEA sextets where line (a) indicates no micro-membrane, line (b) indicates two sextets, and line (c) indicates three sextets. FIG. 2 illustrates the improvement in the stability of the current at 15 mM glucose concentration and at 37° C. when the number of the layers was increased. In the absence of a micro-membrane, 39% of the current was lost in the initial 24 hour period. Application of two sextets (PAc/PAm/PAc/PAm/PAc/PVPEA/PAc/PAm/ PAc/PAm/PAc/PVPEA) reduced the loss to 9%. When three sextets were applied (PAc/PAm/PAc/PAm/PAc/PVPEA/PAc/PAm/PAc/PAm/PAc/PVPEA/PAc/PAm/PAc/PAm/PAc/PVPEA), the 24 hour loss dropped to 5%.

Both urate and the ascorbate anions are electrooxidized at potentials positive of 200 mV (SCE). In the absence of a micro-membrane the electrooxidation current of anionic interferents is disproportionately high when the redox-polymer backbone is a polycation. For example, the ascorbate electrooxidation current at 0.1 mM ascorbate concentration is greater than the glucose electrooxidation current at 1 mM concentration. The cause of the disproportionate electrooxidation of anionic interferents is thought to be due to the scaling of their concentration within the redox polymer with the density of cationic sites. As a result, the permeability of the membrane to anionic interferents (which is the product of concentration and diffusivity) is higher than that of neutral molecules like glucose.

Application of the micro-membrane alleviated the disproportionately large interference by ascorbate and urate, as shown in FIG. 3. At 10 mM glucose concentration, the aggregate increase in current produced by the combination of 0.1 mM ascorbate, 0.2 mM acetaminophen and 0.5 mM urate was less than 5%. The sensitivity of the electrodes to glucose was not changed.

Figure 4:
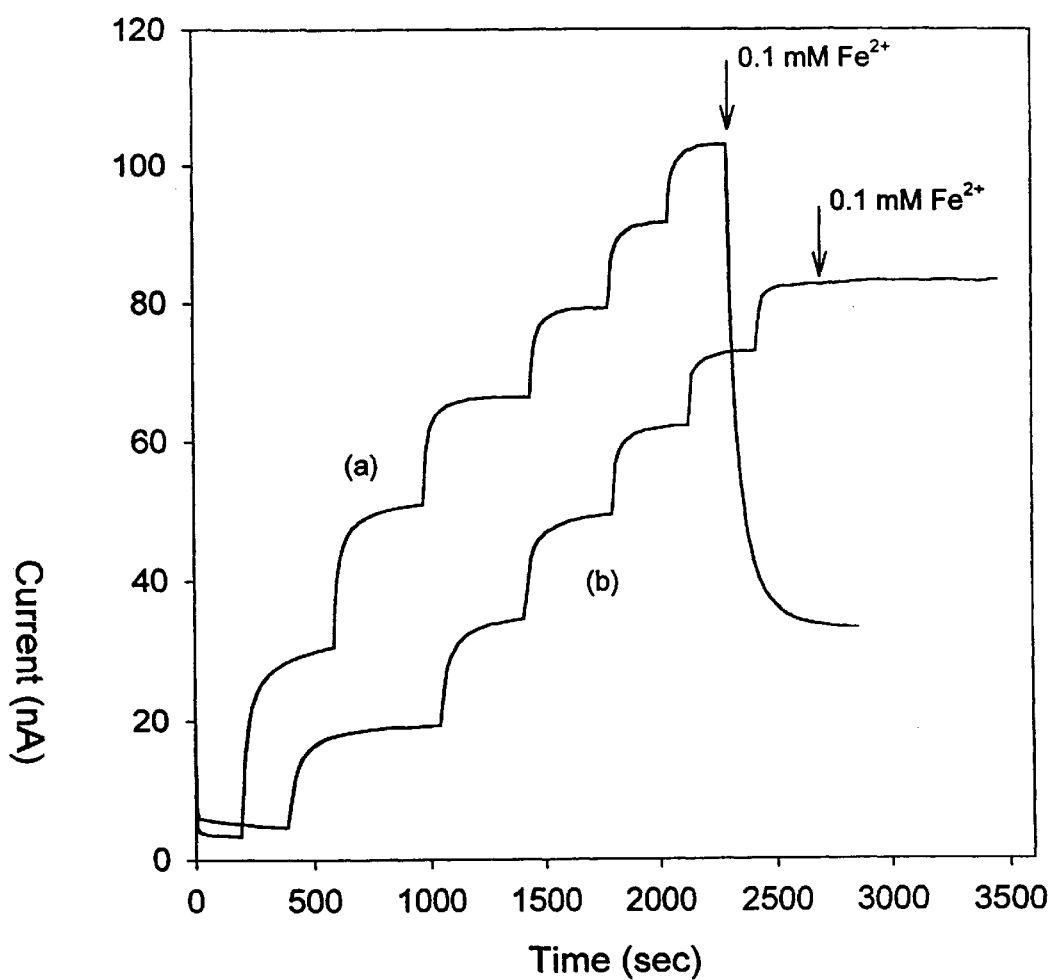
FIG. 4 is a graph illustrating changes in the current upon raising the glucose concentration in 5 mM increments, then adding $Fe^{2+}$ in an amount that in the absence of precipitation of iron phosphate would have raised the concentration of the cation to 0.1 mM with (a) ten PAc/PAm bilayers or (b) three PAc/PAm/PAc/PAm/PAc/PVPEA sextets.

Transition metal ions like $Zn^{2+}$ and $Fe^{2+/3+}$, which are present in serum at <50 μM concentration, can reduce the sensitivity of the "wired" enzyme electrode. The loss is observed even in the presence of 20 mM phosphate, which precipitates most of these ions at neutral pH. Application of multiple bilayers consisting only of PAc/PAm, did not appear to alleviate this loss. The loss was, however, alleviated by incorporating PAc/PVPEA bilayers, which had transition-ion complexing pyridine functions as shown in FIG. 4.

The results show that the following sensor characteristics can be simultaneously provided by a tailored micro-membrane: Linear range, 2 to 30 mM; sensitivity per unit area of 4 to 6 $\mu A cm^{-2} mM^{-1}$, translating to 2 to 3 $nA\ mM^{-1}$ sensitivity for an electrode having a $5\times10^{-4}$ cm$^2$ mass transporting and sensing area; and ≦5% loss in sensitivity in 24 hrs.

Example 3

In Vivo Experiments using the Electrode of Example 1. Male Sprague-Dawley rats, 400–500 g, were pre-anesthetized with halothane (Halocarbon Laboratories, North Augusta, S.C.) and anesthetized by intraperitoneal injection (0.5 mL) of a solution made of equal volumes of acepromazine maleate (10 mg/mL), ketamine (100 mg/mL), and xylazine (20 mg/mL). The animals were shaved about their necks, abdomens, and between their scapulae, and then secured on a homeothermic blanket system (Harvard Apparatus, South Natick, Mass.). A 0.0375-in.-diameter medical grade silicone tube was inserted into the proximal portion of their right external jugular vein and secured with 4-0 silk sutures. A dose of 100 units/kg body weight of heparin solution was then administered, followed by an equal volume of saline to clear the line. A glucose sensor was implanted subcutaneously between the scapulae, using a 22-gauge Per-Q-Cath introducer (Gesco International, San Antonio, Tex.). The sensor was taped to the skin to prevent its movement. A second silicone tubing of ~2 cm length was inserted into the proximal side of the left external jugular vein as a guide, and the second glucose sensor was inserted inside the guide tube. The tube and the sensor were then secured with a microvascular clamp, with the sensor protruding beyond the end of the guide tube. A Ag/AgCl surface skin reference electrode was attached to the animal's abdomen after conductive gel was applied. The sensors and the reference electrode were then connected to an EG&G PARC Model 400 bipotentiostat, the output of which was recorded with a Rustrak Ranger data-logger (Rustrak Ranger, East Greenwich, R.I.). Data collection started 40–60 minutes after the sensors were poised at +450 mV vs. Ag/AgCl. The reference blood samples were collected from the right jugular vein and were analyzed using a YSI Model 2300 glucose analyzer (YSI, Yellow Spring, Ohio).

In each experiment a 50% glucose solution (300 mg/kg) was administered intravenously to induce a rapid rise in glucose concentration. A rapid decline in glucose concentration was then induced by an intravenous insulin injection (regular U-100, 0.5 unit/kg). At the end of the experiment, the rat was euthanized by intravenous sodium pentobarbital injection, consistent with the recommendations of the panel on Euthanasia of the American Veterinary Association. The protocols of the experiments in vivo were approved by the University of Texas Institutional Animal Use and Care Committee.

The experiment was started when the glycemia of the rats was at a steady state, the steady glucose concentration being confirmed by withdrawing three blood samples and their analysis with the YSI analyzer. Two minutes after the third withdrawal a bolus of glucose was injected. The sensors were calibrated in vivo by independently analyzing a single sample of blood about 2 minutes before the injection of the bolus of glucose. FIG. 5(a) shows the variation in the sensor-measured glycemia after boli of glucose and insulin were sequentially administered intravenously. FIG. 5(b) shows the correlation of the sensor readings and the YSI results of FIG. 5(a). The linear regressions for the eight sensors are summarized in Table 1, below. The average correlation coefficient ($r^2$) was 0.960 for the jugular vein sensors and 0.935 for the subcutaneous sensors. The average of the intercept was 0.6 mM±0.6 mM, not differing greatly from the reported −0.79 mM to +0.48 mM range of intercepts of home blood glucose meters used by self-monitoring diabetic patients.

Figure 5:
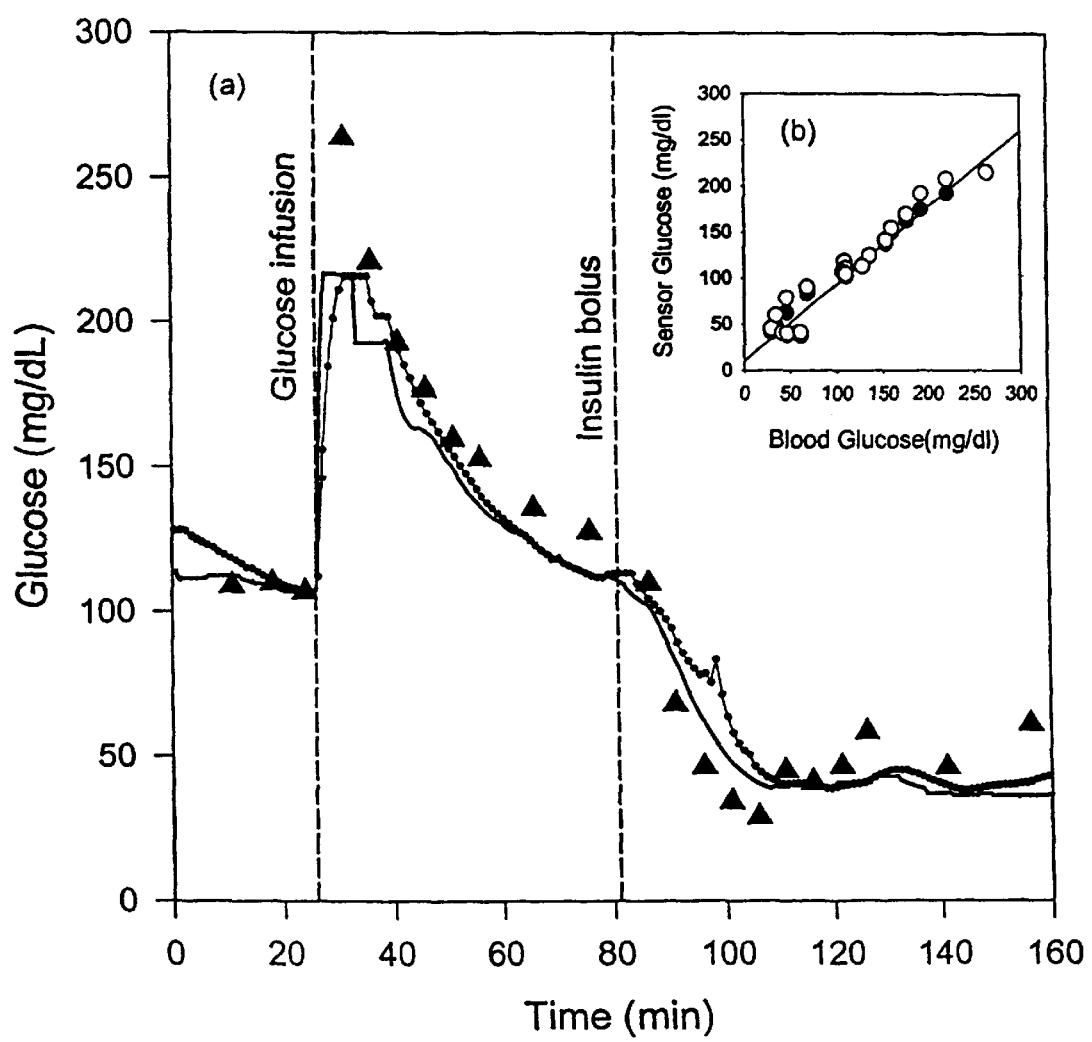
FIG. 5 is a graph depicting in vivo experiments in which the glucose concentration was tracked by sensors with three PAc/PAm/PAc/PAm/PAc/PVPEA sextets. (a) (—) output of the sensor implanted in the jugular vein; ( . . . ) output of the sensor implanted in the intrascapular subcutaneous tissue; (triangles) concentrations of glucose in blood samples withdrawn from the contralateral jugular vein measured with a YSI glucose analyzer; (b) results of linear regression analysis of the data from the two sensors in FIG. 5($a$): in the jugular vein (closed circles) and in the intrascapular subcutaneous tissue (open circles)

As seen in FIG. 5 and in Table 1 the subcutaneous and the jugular-vein implanted sensors with the in situ synthesized micro-membranes accurately track the YSI-glucose analyzer measured blood glucose concentration when calibrated in vivo at one point. The clinical validity of glucose assays is often judged by their position in zones of the Clarke plot. Points in zone A of the Clarke plot represent accurate assays. Points in zone B represent less accurate assays leading to valid clinical decision. Points in Zone C reflect assays leading to inappropriate, though not harmful, clinical decisions. Points in zone D reflect assays leading to the missing of a necessary clinical action (consumption of a glucose-source or insulin-injection) when such action is required. Points in Zone E reflect assays leading to clinical action that are the opposite of the required, such as assays indicating the need to inject insulin when the patient is already hypoglycemic.

Figure 6:
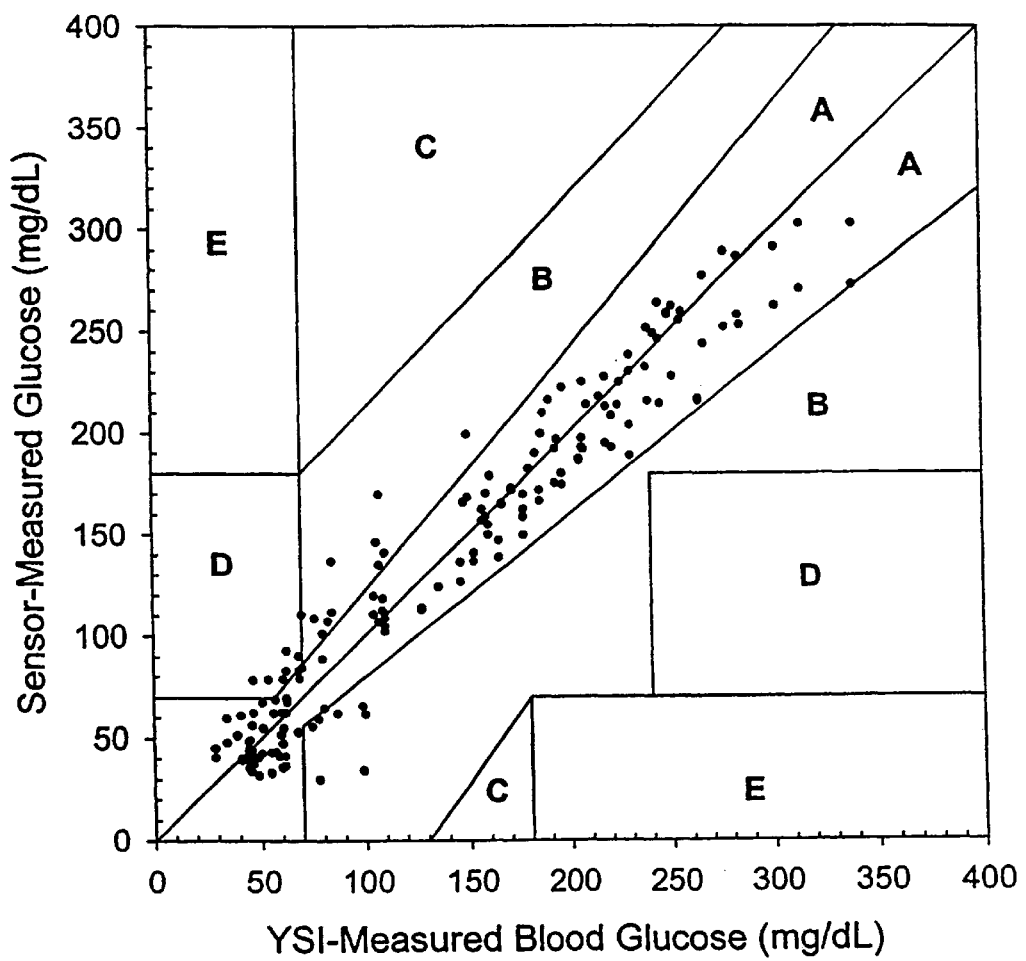
FIG. 6 is a Clarke-type clinical error grid diagram of all data points assuming that the measured glucose concentration does not lag behind the blood glucose concentration at any time.
Figure 7:
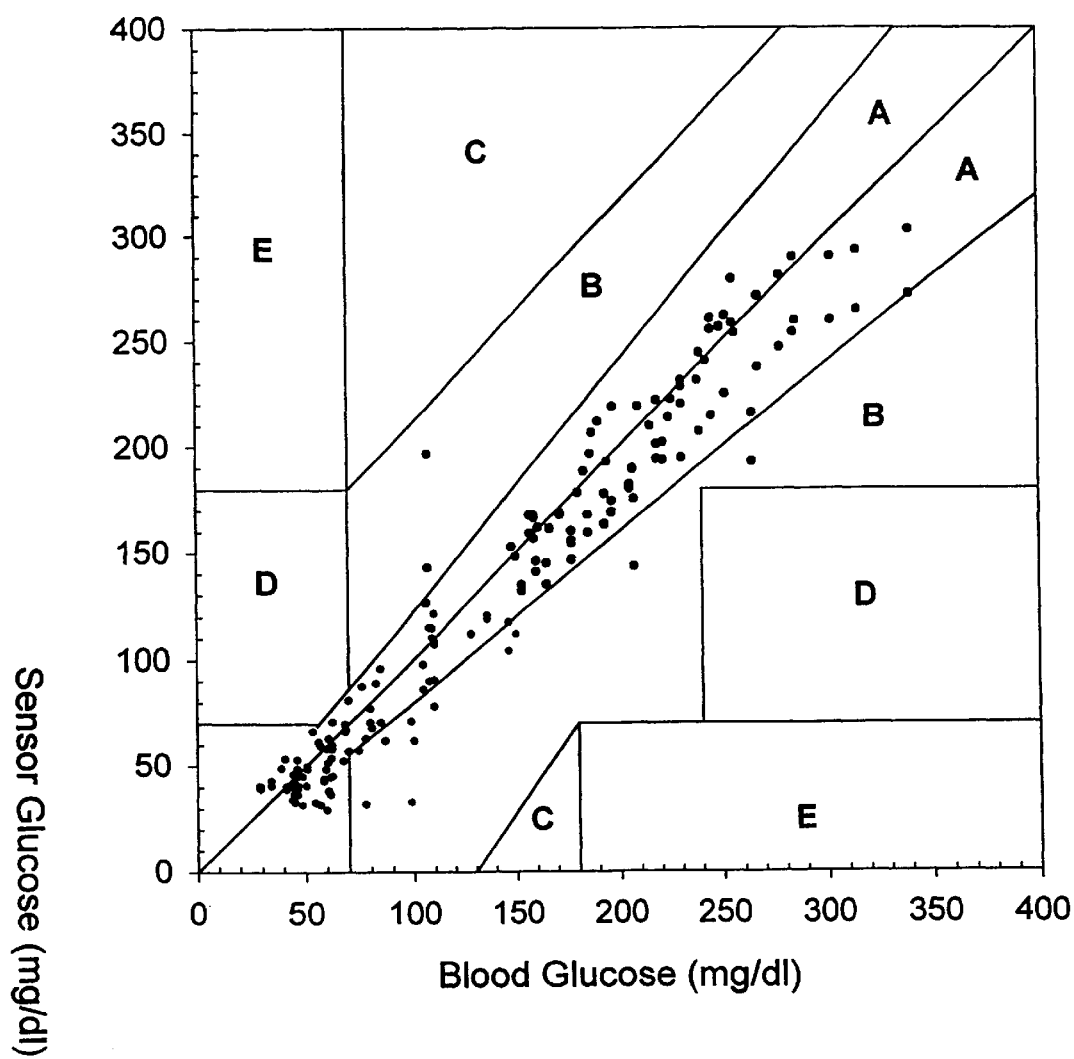
FIG. 7 is a Clarke-type clinical error grid diagram of all data points assuming that the sensor-measured glucose concentration lags by 3 minutes behind the blood glucose concentration in the period of rise after intravenous injection of a bolus of glucose and lags by 9 minutes during the period of decline after intravenous injection of insulin.

In absence of correction for the potential transient difference between the blood and the subcutaneous glucose concentrations during rapid rise or decline periods the Clarke-type error grid analysis (FIG. 6) of the data shows that 95.5% of the points are in the clinically accurate or acceptable zones A or B (Table 2, below). The points in zone D (4.5%) resulted of failure to detect hypoglycemia and originated in periods of rapid decline following intravenous administration of insulin. The fraction of points in zone D was reduced to less than 1% when it was assumed that following insulin injection, but not after glucose injection, the subcutaneous glucose concentration lags behind that of the insulin-injected vein by 9 minutes. Table 3, below, shows that the fraction of points in zones other than zone A of the Clarke plot increased when it was assumed that in the period after intravenous administration of glucose the lag time of the subcutaneous glucose concentration behind that in the glucose-injected vein was greater than 0 to 3 minutes; when no lag or a 3 min lag were assumed all points were in zone A.

The assumptions of a 0 to 3 min lag of the subcutaneous glycemia after glucose injection and of a 9 min lag after insulin injection not only brought all of the 88 points measured with the subcutaneous electrode into zones A and B of the Clarke plot, but also increased the ratio of zone A to zone B points. For the intravenous sensor-measured glycemia, the assumption of a 3 min lag of the contralateral venous glycemia behind that in the injected vein, whether after glucose or insulin injection, brought all points into zones A and B of the Clarke plot (Tables 3 and 4, below). The assumptions of a 9 min lag in the subcutaneous glycemia after insulin injection and of a 3 min lag in the subcutaneous glycemia after glucose injection, as well as in the contralateral venous glycemia after glucose or insulin injection, thus brought 163 of the 176 points (92.6%) into zone A; 13 points being in zone B. Comparison of the values in Table 5, below, with those in Table 1 summarizes the effect of these assumptions on the distribution of points, the slopes, the intercepts, and the percent difference between the YSI and the sensor readings. The sensors with the in-situ assembled micro-membranes accurately measured the glycemia in the jugular vein and in the interstitial subcutaneous fluid.

The present invention should not be considered limited to the particular examples described above, but rather should be understood to cover all aspects of the invention as fairly set out in the attached Claims. Various modifications, equivalent processes, as well as numerous structures to which the present invention may be applicable will be readily apparent to those of skill in the art to which the present invention is directed upon review of the instant specification.

TABLE 1

Results of linear regression analysis of the correlation between the actual glucose blood glucose concentrations and concentrations measured by the implanted sensors[*a]

|  | Slope | Intercept (mg/dL) | $r^2$ | % difference[*b] |
|---|---|---|---|---|
| jugular vein | 0.83 | 9.7 | 0.966 | −3.3 |
| jugular vein | 0.96 | 15.0 | 0.944 | 11.5 |
| jugular vein | 1.02 | −4.2 | 0.957 | −2.7 |
| jugular vein | 0.94 | −0.9 | 0.972 | −9.2 |
| subcutaneous | 0.85 | 13.1 | 0.943 | 3.3 |
| subcutaneous | 0.90 | 30.7 | 0.938 | 12.7 |
| subcutaneous | 0.90 | 3.5 | 0.928 | −9.0 |
| subcutaneous | 0.86 | 15.7 | 0.931 | 0.1 |
| Average | 0.91 ± 0.06 | 10.3 ± 11.1 | 0.947 ± 0.016 | 0.4 ± 8.3 |

[*a]. 22 blood samples were withdrawn and independently analyzed in each experiment.
[*b]. % difference = [Σ((sensor glucose-blood glucose)/blood glucose)]/n

TABLE 2

Clarke-type error grid analysis of all data, without and with assumption of lag.

| | No lag assumed | | Lag assumed | |
|---|---|---|---|---|
| Zone | Data points | % | Data points | % |
| A | 151 | 85.8 | 163 | 92.6 |
| B | 17 | 9.7 | 13 | 7.4 |
| C | 0 | 0.0 | 0 | 0.0 |
| D | 8 | 4.5 | 0 | 0.0 |
| E | 0 | 0.0 | 0 | 0.0 |

*A 3 min lag was assumed, except for the subcutaneous sensors after insulin injection, for which a 9 min lag was assumed.

TABLE 3

Dependence of the distribution of the data points between the zones of the Clarke plot on the assumed lag after injection of glucose.

| Time Delay (mins) | 0 | 3 | 5 | 7 | 9 | 11 |
|---|---|---|---|---|---|---|
| Intravenous Sensors | | | | | | |
| Zone A | 32 | 31 | 30 | 30 | 26 | 24 |
| Zone B | 0 | 1 | 2 | 2 | 6 | 7 |
| Zone D | 0 | 0 | 0 | 0 | 0 | 1 |
| Subcutaneous Sensors | | | | | | |
| Zone A | 32 | 32 | 30 | 30 | 29 | 26 |
| Zone B | 0 | 0 | 2 | 2 | 3 | 6 |
| Zone D | 0 | 0 | 0 | 0 | 0 | 0 |

TABLE 4

Dependence of the distribution of the data points between the zones of the Clarke plot on the assumed lag after injection of insulin.

| Time Delay (mins) | 0 | 3 | 5 | 7 | 9 | 11 |
|---|---|---|---|---|---|---|
| Intravenous Sensors | | | | | | |
| Zone A | 35 | 41 | 40 | 38 | 34 | 33 |
| Zone B | 7 | 3 | 4 | 6 | 10 | 11 |
| Zone D | 2 | 0 | 0 | 0 | 0 | 0 |
| Subcutaneous Sensors | | | | | | |
| Zone A | 28 | 34 | 36 | 35 | 37 | 34 |
| Zone B | 10 | 7 | 6 | 7 | 7 | 10 |
| Zone D | 6 | 3 | 2 | 2 | 0 | 0 |

TABLE 5

Results of linear regression analyses of the correlation between the YSI-measured venous glycemia and the sensor-measured glycemia assuming the optimal lag times.*

| | Slope | Intercept, mg/dL | $r^2$ | % Difference |
|---|---|---|---|---|
| jugular vein | 0.78 | 9.8 | 0.964 | 12.5 |
| jugular vein | 0.99 | 7.3 | 0.968 | 9.9 |
| jugular vein | 1.03 | −11.6 | 0.981 | 5.7 |
| jugular vein | 0.94 | −5.8 | 0.980 | 9.6 |
| average | 0.94 ± 0.07 | 2.4 ± 8.6 | 0.973 ± 0.007 | 9.4 ± 1.9 |
| subcutaneous | 0.85 | 7.5 | 0.947 | 10.7 |
| subcutaneous | 0.97 | −23.8 | 0.954 | 16.9 |
| subcutaneous | 0.97 | 3.8 | 0.975 | 5.7 |
| subcutaneous | 0.88 | 2.3 | 0.973 | 9.0 |
| average | 0.92 ± 0.05 | −2.5 ± 7.2 | 0.962 ± 0.012 | 10.6 ± 3.0 |
| average (all data) | 0.93 ± 0.08 | −1.3 ± 11.6 | 0.968 ± 0.012 | 10.0 ± 3.6 |

*3 min lag for the contra-lateral venous and the subcutaneous glycemia after injection of glucose; 3 min lag of the contra-lateral venous glycemia after injection of insulin; 9 min lag of the subcutaneous glycemia after injection of insulin.

What is claimed is:

1. A sensor, comprising:
   a sensing layer comprising an osmium redox polymer disposed on a substrate;
   a multilayer flux-limiting membrane comprising a first layer, any subsequent layers, and a polyanionic last layer disposed over the sensing layer, the first layer disposed on and binding to the sensing layer, at least one of the first layer and any subsequent layer being polycationic and comprising pyridine, each layer disposed on and bound to the immediately preceding layer of the membrane.

2. The sensor of claim 1, wherein the sensor has an active area of 0.1 cm² or less.

3. The sensor of claim 1, wherein the active area is in a range of $10^{-2}$ cm² to $10^{-8}$ cm².

4. The sensor of claim 1, wherein the active area is in a range of $10^{-3}$ cm² to $10^{-6}$ cm².

5. The sensor of claim 1, wherein the sensing layer comprises an enzyme.

6. The sensor of claim 1, wherein the substrate comprises an electrode upon which the sensing layer is disposed.

7. The sensor of claim 1, wherein the substrate comprises an optical fiber upon which the sensing layer is disposed.

8. The sensor of claim 7, wherein the sensing layer is disposed on a tip of the optical fiber.

9. The sensor of clam 1, wherein the osmium redox polymer comprises a non-leachable redox compound.

10. The sensor of claim 1, wherein the multilayer membrane comprises the polycationic layer adjacent the polyanionic last layers.

11. The sensor of claim 1, wherein the sensor is adapted for implantation of at least a portion of the sensor in an animal.

12. The sensor of claim 1, wherein the sensor is adapted for subcutaneous implantation of at least a portion of the sensor in an animal.

13. The sensor of claim 1, further comprising a biocompatible layer disposed over the multilayer membrane.

14. The sensor of claim 1, wherein at least one of the layers of the multilayer membrane comprises functional groups that can capture transition metal ions.

15. The sensor of claim 1, wherein the membrane is configured and arranged to reduce flux of an analyte to the sensing layer.

16. The sensor of claim 1, wherein the membrane is configured and arranged to reduce flux of at least one interferent to the sensing layer.

17. The sensor of claim 1, wherein the multilayer membrane comprises the first layer, the last layer, and one subsequent layer.

18. The sensor of claim 1, wherein the multilayer membrane comprises the first layer, the last layer, and at least four subsequent layers.

19. A method of making a sensor, the method comprising steps of:

disposing a sensing layer on a surface; and forming a membrane over the sensing layer by chemisorbing, in an alternating and binding manner, at least three layers alternating between polyanionic layers and polycationic layers comprising pyridine, with a last layer being a polyanionic layer.

20. The method of claim 19, further comprising disposing a biocompatible layer over the membrane.

21. A method of making a sensor, the method comprising steps of:

disposing a sensing layer on a substrate;

disposing and binding a first membrane layer on the sensing layer;

optionally disposing one or more subsequent membrane layers on the first membrane layer; and disposing a polyanionic last membrane layer, wherein at least one of the first membrane layer and any optional subsequent membrane layer is polycationic and comprises pyridine.

22. The method of claim 21, wherein the membrane layers are bound to the sensing layer or any protecting membrane layer by chemisorption or reactive adsorption.

23. The method of claim 22, further comprising rinsing after disposing at least one of the first membrane layer or any subsequent membrane layers.

* * * * *

UNITED STATES PATENT AND TRADEMARK OFFICE
CERTIFICATE OF CORRECTION

PATENT NO. : 6,746,582 B2
DATED : June 8, 2004
INVENTOR(S) : Heller et al.

It is certified that error appears in the above-identified patent and that said Letters Patent is hereby corrected as shown below:

Column 16,
Line 9, "or any protecting membrane" should read -- or any preceding membrane --

Signed and Sealed this

Seventeenth Day of August, 2004

JON W. DUDAS
*Acting Director of the United States Patent and Trademark Office*